United States Patent
Moffitt et al.

(10) Patent No.: US 12,427,324 B2
(45) Date of Patent: Sep. 30, 2025

(54) PRESCRIBED NEUROMODULATION DOSE DELIVERY

(71) Applicant: Boston Scientific Neuromodulation Corporation, Valencia, CA (US)

(72) Inventors: Michael A. Moffitt, Solon, OH (US); Ismael Huertas Fernandez, Madrid (ES)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/363,405

(22) Filed: Aug. 1, 2023

(65) Prior Publication Data
US 2023/0405342 A1 Dec. 21, 2023

Related U.S. Application Data

(63) Continuation of application No. 16/741,258, filed on Jan. 13, 2020, now abandoned, which is a
(Continued)

(51) Int. Cl.
*A61N 1/372* (2006.01)
*A61N 1/36* (2006.01)
(Continued)

(52) U.S. Cl.
CPC ..... *A61N 1/37247* (2013.01); *A61N 1/36071* (2013.01); *A61N 1/3615* (2013.01);
(Continued)

(58) Field of Classification Search
CPC ............ A61N 1/37247; A61N 1/36071; A61N 1/3615; A61N 1/36167; A61N 1/3787;
(Continued)

(56) References Cited

U.S. PATENT DOCUMENTS 6,108,579 A 8/2000 Snell et al.
6,181,969 B1 1/2001 Gord
(Continued)

FOREIGN PATENT DOCUMENTS

CN 202933390 5/2013
EP 2243510 B1 4/2014
(Continued)

OTHER PUBLICATIONS

L. Kapural et al., "Novel 10-kHz High-frequency Therapy (HF10 Therapy) Is Superior to Traditional Low-frequency Spinal Cord Stimulation for the Treatment of Chronic Back and Leg Pain," Anesthesiology 2015; 123:851-60 (Oct. 2015).
(Continued)

*Primary Examiner* — Amanda K Hulbert
*Assistant Examiner* — Philip C Edwards
(74) *Attorney, Agent, or Firm* — Lewis & Reese, PLLC

(57) ABSTRACT

Methods and systems for providing stimulation therapy are disclosed. Embodiments of the system include an implantable stimulator and an external controller configured to control the implantable stimulator. A clinician can prescribe a set amount of stimulation therapy to a patient. The external controller is programmed with the prescription. As the patient uses the external controller and the stimulator device the external controller tracks the amount of stimulation the patient uses. Once the patient has used all of the prescribed therapy the patient may return to the clinician for a follow-up appointment.

16 Claims, 8 Drawing Sheets

Related U.S. Application Data continuation-in-part of application No. 16/738,786, filed on Jan. 9, 2020, now Pat. No. 11,951,314, which is a continuation-in-part of application No. 16/657,560, filed on Oct. 18, 2019, which is a continuation-in-part of application No. 16/460,640, filed on Jul. 2, 2019, and a continuation-in-part of application No. 16/460,655, filed on Jul. 2, 2019, now Pat. No. 11,338,127, and a continuation-in-part of application No. 16/100,904, filed on Aug. 10, 2018, now Pat. No. 10,576,282.

(60) Provisional application No. 62/916,958, filed on Oct. 18, 2019, provisional application No. 62/803,330, filed on Feb. 8, 2019, provisional application No. 62/693,543, filed on Jul. 3, 2018, provisional application No. 62/544,656, filed on Aug. 11, 2017.

(51) Int. Cl.
*A61N 1/378* (2006.01)
*G16H 20/40* (2018.01)
*G16H 40/67* (2018.01)

(52) U.S. Cl.
CPC ....... *A61N 1/36167* (2013.01); *A61N 1/3787* (2013.01); *G16H 20/40* (2018.01); *G16H 40/67* (2018.01)

(58) Field of Classification Search
CPC .... A61N 1/36062; G16H 20/40; G16H 40/67; G16H 40/63; G16H 20/30
See application file for complete search history.

(56) References Cited

U.S. PATENT DOCUMENTS

| | | |
|---|---|---|
| 6,516,227 B1 | 2/2003 | Meadows et al. |
| 7,359,751 B1 | 4/2008 | Erickson et al. |
| 7,603,177 B2 | 10/2009 | Sieracki et al. |
| 8,180,451 B2 | 5/2012 | Hickman et al. |
| 8,359,102 B2 | 1/2013 | Alataris et al. |
| 8,515,546 B2 | 8/2013 | Goddard et al. |
| 8,606,362 B2 | 12/2013 | He et al. |
| 8,620,436 B2 | 12/2013 | Parramon et al. |
| 8,712,533 B2 | 4/2014 | Alataris et al. |
| 8,792,988 B2 | 7/2014 | Alataris et al. |
| 9,259,574 B2 | 2/2016 | Aghassian et al. |
| 9,327,125 B2 | 5/2016 | Alataris et al. |
| 9,333,357 B2 | 5/2016 | Alataris et al. |
| 9,446,243 B2 | 9/2016 | Marnfeldt et al. |
| 9,480,842 B2 | 11/2016 | Alataris et al. |
| 9,789,252 B2 | 10/2017 | Gerber et al. |
| 2010/0023090 A1 | 1/2010 | Jaax et al. |
| 2010/0274312 A1 | 10/2010 | Alataris et al. |
| 2011/0137371 A1* | 6/2011 | Giftakis ................ A61B 5/293 607/45 |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2012/0277621 A1 | 11/2012 | Gerber et al. |
| 2013/0053923 A1 | 2/2013 | Jaax et al. |
| 2013/0110195 A1 | 5/2013 | Fletcher et al. |
| 2013/0268026 A1 | 10/2013 | Rao et al. |
| 2014/0277251 A1 | 9/2014 | Gerber et al. |
| 2014/0330336 A1 | 11/2014 | Errico et al. |
| 2014/0364919 A1 | 12/2014 | Doan |
| 2015/0005680 A1* | 1/2015 | Lipani ..................... A61F 7/12 607/113 |
| 2015/0080982 A1 | 3/2015 | Funderburk |
| 2015/0182749 A1* | 7/2015 | Fang .................. A61N 1/0551 607/46 |
| 2015/0231402 A1 | 8/2015 | Aghassian |
| 2015/0335893 A1 | 11/2015 | Parker |
| 2015/0360038 A1 | 12/2015 | Zottola et al. |
| 2016/0082265 A1 | 3/2016 | Moffitt et al. |
| 2016/0114166 A1 | 4/2016 | Kaula et al. |
| 2016/0144183 A1 | 5/2016 | Marnfeldt |
| 2016/0158538 A1 | 6/2016 | Guarraia et al. |
| 2016/0158551 A1 | 6/2016 | Kent et al. |
| 2016/0175594 A1* | 6/2016 | Min .................. A61N 1/36171 607/72 |
| 2016/0317815 A1 | 11/2016 | Doan et al. |
| 2016/0361543 A1 | 12/2016 | Kaula et al. |
| 2016/0367822 A1 | 12/2016 | Parramon |
| 2017/0056642 A1 | 3/2017 | Moffitt et al. |
| 2017/0080234 A1* | 3/2017 | Gillespie ............ A61N 1/37247 |
| 2017/0106197 A1 | 4/2017 | Wechter et al. |
| 2017/0128725 A1 | 5/2017 | Kim et al. |
| 2017/0165490 A1 | 6/2017 | Wechter |
| 2017/0173335 A1 | 6/2017 | Min et al. |
| 2017/0189685 A1 | 7/2017 | Steinke et al. |
| 2017/0197086 A1* | 7/2017 | Howard .................. H04W 4/60 |
| 2017/0312526 A1 | 11/2017 | Steinke et al. |
| 2018/0043172 A1 | 2/2018 | Serrano Carmona |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0078756 A1 | 3/2018 | Bennett et al. |
| 2018/0104493 A1 | 4/2018 | Doan et al. |
| 2018/0140831 A1 | 5/2018 | Feldman et al. |
| 2018/0193651 A1 | 7/2018 | Annoni et al. |
| 2019/0046800 A1 | 2/2019 | Doan et al. |
| 2019/0083796 A1 | 3/2019 | Weerakoon et al. |
| 2019/0175915 A1 | 6/2019 | Brill et al. |
| 2019/0209844 A1 | 7/2019 | Esteller et al. |
| 2019/0290900 A1 | 9/2019 | Esteller et al. |
| 2019/0298992 A1 | 10/2019 | Zhang et al. |
| 2019/0329024 A1 | 10/2019 | Kothandaraman et al. |
| 2019/0329025 A1 | 10/2019 | Moffitt et al. |
| 2019/0329039 A1 | 10/2019 | Marnfeldt et al. |
| 2019/0344083 A1 | 11/2019 | Marnfeldt et al. |
| 2019/0366104 A1 | 12/2019 | Doan et al. |
| 2020/0009367 A1 | 1/2020 | Huertas Fernandez et al. |
| 2020/0009394 A1 | 1/2020 | Huertas Fernandez et al. |
| 2020/0046980 A1 | 2/2020 | Moffitt et al. |
| 2022/0323764 A1 | 10/2022 | Esteller et al. |

FOREIGN PATENT DOCUMENTS

| | | |
|---|---|---|
| EP | 2701793 B1 | 2/2015 |
| EP | 2923727 | 9/2015 |
| WO | 87/07511 | 12/1987 |
| WO | 2007/136694 | 11/2007 |
| WO | 2017/106539 | 6/2017 |

OTHER PUBLICATIONS

S. Thomson et al., "The PROCO Randomised Controlled Trial: Effects of Pulse Rate On Clinical Outcomes in Kilohertz Frequency Spinal Cord Stimulation—A Multicentre, Double-blind, Crossover Study," presented at the International Neuromodulation Society (INS) Meeting on May 31, 2017.

E.C. Celik et al., "The effect of low-frequency TENS in the treatment of neuropathic pain in patients with spinal cord injury," Spinal Cord 51:34-337 (2013).

Y. Maeda et al., "Low frequencies, but not high frequencies of bi-polar spinal cord stimulation reduce cutaneous and muscle hyperalgesia induced by nerve injury," Pain 138:143-152 (2008).

S. Thomson et al., "Neural Dosing and Energy Requirements in Kilohertz Frequency Spinal Cord Stimulation (SCS)," poster presented at the International Neuromodulation Society (INS) Meeting on May 31, 2017.

S. Paz et al., "Improved Efficacy of SCS Implants Using Multiple Waveforms and Field Shape Options," poster presented at the International Neuromodulation Society (INS) Meeting on May 31, 2017.

S. Paz et al., "Evaluation of Customized Field Shape for Subperception SCS in a Case Series of Chronic Pain Patients," poster presented at the North American Neuromodulation Society (NANS) Meeting on Jan. 11-14, 2018.

(56) References Cited

OTHER PUBLICATIONS

S.J. Thomson et al., "Effects of Rate on Analgesia in Kilohertz Frequency Spinal Cord Stimulation: Results of the PROCO Randomized Controlled Trial," Neuromodulation: Technology at the Neural Interface, vol. 21(1), pp. 67-76 (2018) (published on-line Dec. 8, 2017).

J.M. North et al., "Clinical Outcomes of 1 kHz Subperception Spinal Cord Stimulation in Implanted Patients With Failed Paresthesia-Based Stimulation: Results of a Prospective Randomized Controlled Trial," Neuromodulation: Technology at the Neural Interface, vol. 19(7), pp. 731-737 (2016).

Yearwood, Thomas, et al., Handout titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood, Thomas, et al., Poster titled "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 7 pages.

Yearwood, Thomas, "Neuropathic Extremity Paid and Spinal Cord Stimulation," Pain Medicine, vol. 7, No. S1, 2006, 6 pages.

International Search Report and Written Opinion regarding corresponding PCT Application No. PCT/US2020/013346, mailed Apr. 21, 2020.

Miller JP, Eldabe S, Buchser E, Johanek LM, Guan Y, Linderoth B, "Parameters of Spinal Cord Stimulation and their Role in Electrical Charge Delivery: A Review," Neuromodulation, Jun. 2016, 19(4): 373-84. doi: 10.1111/ner.12438. Epub May 6, 2016. PMID: 27150431. (Year: 2016).

Deer et al., "The Appropriate Use of Neurostimulation: Avoidance and Treatment of Complications of Neurostimulation Therapies for the Treatment of Chronic Pain," Neuromodulation: Technology at the Neural Interface, vol. 17, Issue 6, 2014, pp. 571-598 (Year: 2014).

Extended European Search Report regarding corresponding European Patent Application Serial No. 23178615.3, mailed Oct. 6, 2023.

Cogan, Stuart F., "Neural Stimulation and Recording Electrodes," Annual Review of Biomedical Engineering, vol. 10, No. 1, Aug. 1, 2008, pp. 275-309.

Extended European Search Report regarding corresponding European patent application No. 24210637.5, mailed Apr. 7, 2025.

\* cited by examiner

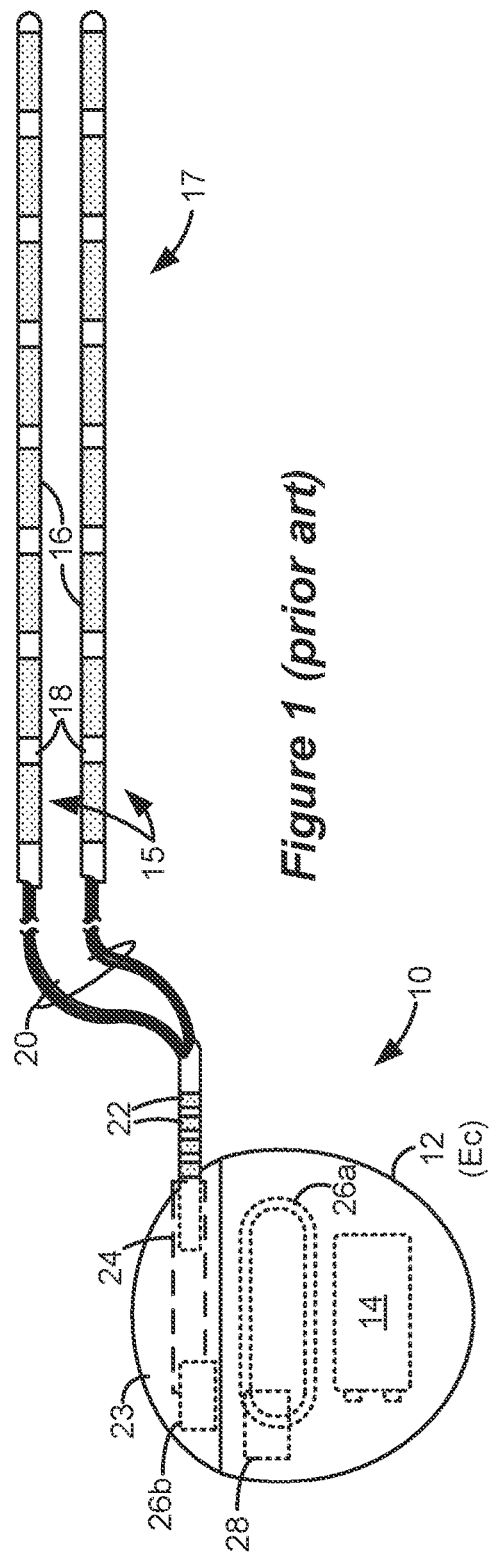
*Figure 1 (prior art)*
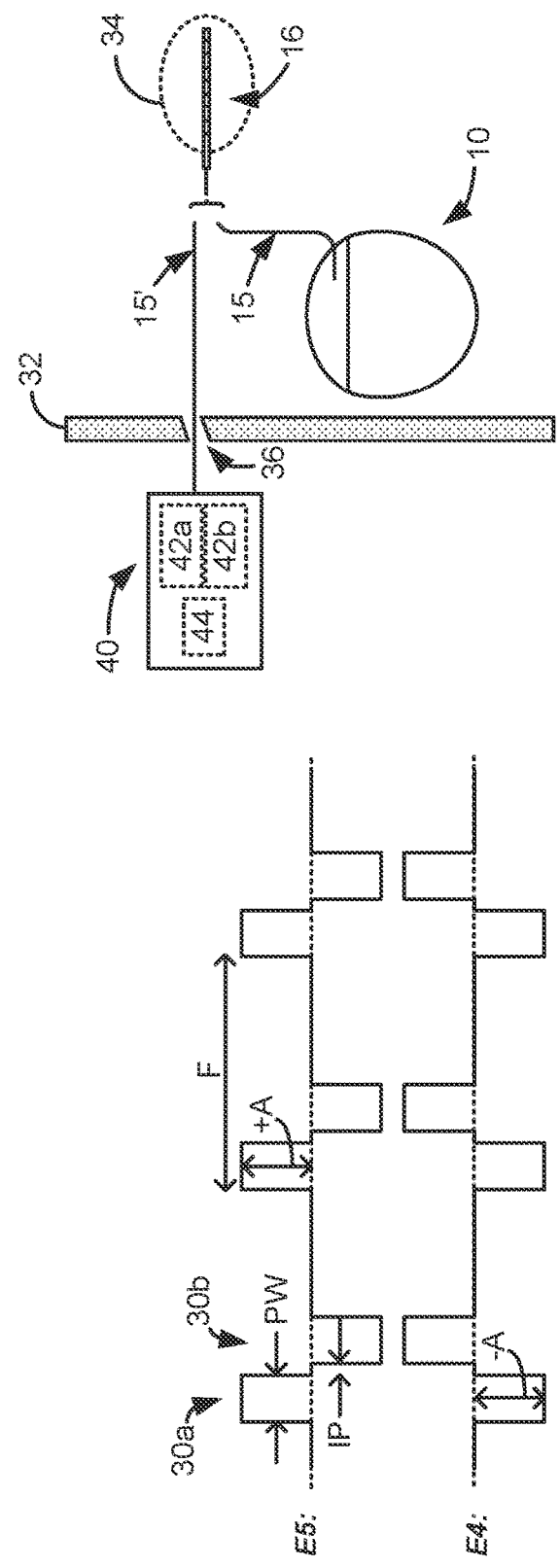
*Figure 3 (prior art)*
*Figure 2 (prior art)*

PRESCRIBED NEUROMODULATION DOSE DELIVERY

CROSS REFERENCE TO RELATED APPLICATIONS

This application is a continuation application of U.S. patent application Ser. No. 16/741,258, filed Jan. 13, 2020, which is a non-provisional application of U.S. Provisional Patent Application Ser. No. 62/916,958, filed Oct. 18, 2019. U.S. patent application Ser. No. 16/741,258 is also a continuation-in-part of U.S. patent application Ser. No. 16/738,786, filed Jan. 9, 2020, which is a continuation-in-part of U.S. patent application Ser. No. 16/657,560, filed Oct. 18, 2019, which is a continuation-in-part of;

U.S. patent application Ser. No. 16/100,904, filed Aug. 10, 2018 (now USP which is a non-provisional application of U.S. Provisional Patent Application Serial Nos. 62/693,543, filed Jul. 3, 2018, and 62/544,656, filed Aug. 11, 2017;

U.S. patent application Ser. No. 16/460,640, filed Jul. 2, 2019, which is a non-provisional application of U.S. Provisional Patent Application Ser. No. 62/803,330, filed Feb. 8, 2019; and U.S. patent application Ser. No. 16/460,655, filed Jul. 2, 2019 (now U.S. Pat. No. 11,338,127), which is a non-provisional application of U.S. Provisional Patent Application Ser. No. 62/803,330, filed Feb. 8, 2019.

Priority is claimed to these above-referenced applications, and all are incorporated by reference in their entireties.

FIELD OF THE INVENTION

This application relates to Implantable Medical Devices (IMDs), generally, Spinal Cord Stimulators, more specifically, and to methods of control of such devices.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include the amplitude of the pulses (A; whether current or voltage); the frequency (F) and pulse width (PW) of the pulses; the electrodes 16 (E) activated to provide such stimulation; and the polarity (P) of such active electrodes, i.e., whether active electrodes are to act as anodes (that source current to the tissue) or cathodes (that sink current from the tissue). These stimulation parameters taken together comprise a stimulation program that the IPG 10 can execute to provide therapeutic stimulation to a patient.

In the example of FIG. 2, electrode E5 has been selected as an anode, and thus provides pulses which source a positive current of amplitude +A to the tissue. Electrode E4 has been selected as a cathode, and thus provides pulses which sink a corresponding negative current of amplitude −A from the tissue. This is an example of bipolar stimulation, in which only two lead-based electrodes are used to provide stimulation to the tissue (one anode, one cathode). However, more than one electrode may act as an anode at a given time, and more than one electrode may act as a cathode at a given time (e.g., tripole stimulation, quadripole stimulation, etc.).

The pulses as shown in FIG. 2 are biphasic, comprising a first phase 30a, followed quickly thereafter by a second phase 30b of opposite polarity. As is known, use of a biphasic pulse is useful in active charge recovery. For example, each electrodes' current path to the tissue may include a serially-connected DC-blocking capacitor, see, e.g., U.S. Patent Application Publication 2016/0144183, which will charge during the first phase 30a and discharged (be recovered) during the second phase 30b. In the example shown, the first and second phases 30a and 30b have the same duration and amplitude (although opposite polarities), which ensures the same amount of charge during both phases. However, the second phase 30b may also be charged balance with the first phase 30a if the integral of the amplitude and durations of the two phases are equal in magnitude, as is well known. The width of each pulse, PW, is defined here as the duration of first pulse phase 30a, although pulse width could also refer to the total duration of the first and second pulse phases 30a and 30b as well. Note that an interphase period (IP) during which no stimulation is provided may be provided between the two phases 30a and 30b.

IPG 10 includes stimulation circuitry 28 that can be programmed to produce the stimulation pulses at the electrodes as defined by the stimulation program. Thus, the IPG 10 acts as a power supply to deliver power to the electrodes for providing stimulation to the patient. Stimulation circuitry 28 can for example comprise the circuitry described in U.S. Patent Application Publications 2018/0071513 and 2018/0071520, or described in U.S. Pat. Nos. 8,606,362 and 8,620,436. These references are incorporated herein by reference.

FIG. 3 shows an external trial stimulation environment that may precede implantation of an IPG 10 in a patient. During external trial stimulation, stimulation can be tried on a prospective implant patient without going so far as to implant the IPG 10. Instead, one or more trial leads 15' are implanted in the patient's tissue 32 at a target location 34, such as within the spinal column as explained earlier. The proximal ends of the trial lead(s) 15' exit an incision 36 and are connected to an External Trial Stimulator (ETS) 40. The ETS 40 generally mimics operation of the IPG 10, and thus can provide stimulation pulses to the patient's tissue as explained above. See, e.g., U.S. Pat. No. 9,259,574, disclosing a design for an ETS. The ETS 40 is generally worn externally by the patient for a short while (e.g., two weeks), which allows the patient and his clinician to experiment with different stimulation parameters to try and find a stimulation program that alleviates the patient's symptoms (e.g., pain). If external trial stimulation proves successful, trial lead(s) 15' are explanted, and a full IPG 10 and lead(s) 15 are implanted as described above; if unsuccessful, the trial lead(s) 15' are simply explanted.

Like the IPG 10, the ETS 40 can include one or more antennas to enable bi-directional communications with external devices, explained further with respect to FIG. 4. Such antennas can include a near-field magnetic-induction coil antenna 42a, and/or a far-field RF antenna 42b, as described earlier. ETS 40 may also include stimulation circuitry 44 able to form the stimulation pulses in accordance with a stimulation program, which circuitry may be similar to or comprise the same stimulation circuitry 28 present in the IPG 10. ETS 40 may also include a battery (not shown) for operational power.

FIG. 4 shows various external devices that can wirelessly communicate data with the IPG 10 and the ETS 40, including a patient, hand-held external controller 45, and a clinician programmer 50. Both of devices 45 and 50 can be used to send a stimulation program to the IPG or ETS 40—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 40 is currently executing. Devices 45 and 50 may also receive information from the IPG 10 or ETS 40, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 40, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 40. For example, the external controller 45 can have a near-field magnetic-induction coil antenna 47a capable of wirelessly communicating with the coil antenna 26a or 42a in the IPG 10 or ETS 40. The external controller 45 can also have a far-field RF antenna 47b capable of wirelessly communicating with the RF antenna 26b or 42b in the IPG 10 or ETS 40.

The external controller 45 can also have control circuitry 48 such as a microprocessor, microcomputer, an FPGA, other digital logic structures, etc., which is capable of executing instructions an electronic device. Control circuitry 48 can for example receive patient adjustments to stimulation parameters, and create a stimulation program to be wirelessly transmitted to the IPG or ETS 40.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS can depend on the type of antennas included in those devices. If the patient's IPG 10 or ETS includes a coil antenna 26a or 42a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 40.

If the IPG 10 or ETS 40 includes an RF antenna 26b or 42b, the wand 54, the computing device 51, or both, can likewise include an RF antenna 56b to establish communication with the IPG 10 or ETS 40 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 40, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by control circuitry 70 such as a microprocessor, microcomputer, an FPGA, other digital logic structures, etc., which is capable of executing programs in a computing device. Such control circuitry 70, in addition to executing the clinician programmer software 66 and rendering the GUI 64, can also enable communications via antennas 56a or 56b to communicate stimulation parameters chosen through the GUI 64 to the patient's IPG 10.

A portion of the GUI 64 is shown in one example in FIG. 5. One skilled in the art will understand that the particulars of the GUI 64 will depend on where clinician programmer software 66 is in its execution, which will depend on the GUI selections the clinician has made. FIG. 5 shows the GUI 64 at a point allowing for the setting of stimulation parameters for the patient and for their storage as a stimulation program. To the left a program interface 72 is shown, which as explained further in the '038 Publication allows for naming, loading and saving of stimulation programs for the patient. Shown to the right is a stimulation parameters interface 82, in which specific stimulation parameters (A, D, F, E, P) can be defined for a stimulation program. Values for stimulation parameters relating to the shape of the waveform (A; in this example, current), pulse width (PW), and frequency (F) are shown in a waveform parameter interface 84, including buttons the clinician can use to increase or decrease these values.

Stimulation parameters relating to the electrodes 16 (the electrodes E activated and their polarities P), are made adjustable in an electrode parameter interface 86. Electrode stimulation parameters are also visible and can be manipulated in a leads interface 92 that displays the leads 15 (or 15') in generally their proper position with respect to each other, for example, on the left and right sides of the spinal column. A cursor 94 (or other selection means such as a mouse pointer) can be used to select a particular electrode in the leads interface 92. Buttons in the electrode parameter interface 86 allow the selected electrode (including the case electrode, Ec) to be designated as an anode, a cathode, or off. The electrode parameter interface 86 further allows the relative strength of anodic or cathodic current of the selected electrode to be specified in terms of a percentage, X. This is particularly useful if more than one electrode is to act as an anode or cathode at a given time, as explained in the '038 Publication. In accordance with the example waveforms shown in FIG. 2, as shown in the leads interface 92, electrode E5 has been selected as the only anode to source current, and this electrode receives X=100% of the specified anodic current, +A Likewise, electrode E4 has been selected as the only cathode to sink current, and this electrode receives X=100% of that cathodic current, −A.

The GUI 64 as shown specifies only a pulse width PW of the first pulse phase 30a. The clinician programmer software 66 that runs and receives input from the GUI 64 will nonetheless ensure that the IPG 10 and ETS 40 are programmed to render the stimulation program as biphasic pulses if biphasic pulses are to be used. For example, the clinician programming software 66 can automatically determine durations and amplitudes for both of the pulse phases 30a and 30b (e.g., each having a duration of PW, and with opposite polarities +A and −A). An advanced menu 88 can also be used (among other things) to define the relative durations and amplitudes of the pulse phases 30a and 30b, and to allow for other more advance modifications, such as setting of a duty cycle (on/off time) for the stimulation pulses, and a ramp-up time over which stimulation reaches its programmed amplitude (A), etc. A mode menu 90 allows the clinician to choose different modes for determining stimulation parameters. For example, as described in the '038 Publication, mode menu 90 can be used to enable electronic trolling, which comprises an automated programming mode that performs current steering along the electrode array by moving the cathode in a bipolar fashion.

While GUI 64 is shown as operating in the clinician programmer 50, the user interface of the external controller 45 may provide similar functionality.

FIG. 6 shows an alternative embodiment of an implantable SCS system 600 comprising an implanted electrode lead 602 having electrodes 16 disposed thereon. The SCS system 600 does not use an implanted IPG to provide power for electrical stimulation. Instead, power is provided via radio frequency (RF) transmission through the patient's tissue 32 from an external power supply (EPS) 604. The EPS has an RF antenna 606 configured to transmit RF power and the implanted lead 602 comprises an antenna 608 configured to receive the RF power. The implanted lead 602 also has simple circuitry (not shown) configured to rectify the RF power and generate pulses. As with the IPG system described above, the RF-powered system 600 may use an external controller 45 to control and transmit stimulation parameters. However, in the system 600, the external controller 45 provides stimulation parameters to the EPS 604, rather than to an implanted IPG. While the EPS 604 and the external controller 45 are illustrated as separate units in FIG. 6, the EPS 604 and the external controller 45 may be combined as a single unit. The illustrated SCS system 600 has an advantage over the system illustrated in FIG. 1 in that the system 600 does not require a surgical procedure to implant an IPG (10, FIG. 1) and tunnel lead wires (20, FIG. 1) between the IPG and the electrode leads. However, a disadvantage of the system 600 (FIG. 6) is that the patient must position the EPS 604 near their tissue any time that they wish to receive stimulation. The EPS 604 may be carried in a belt, pouch or other carrying device, for example. Systems as shown in FIG. 6, which rely on RF energy provided by an EPS are referred to herein as "RF systems."

SUMMARY

A method of providing a prescribed amount of stimulation to a patient using an implantable stimulator device that is implantable in the patient and an external controller configured to control the implantable stimulator device is disclosed herein. According to some embodiments, the method comprises: receiving a prescription, wherein the prescription quantifies the prescribed amount of stimulation to be provided by the implantable stimulator device, using the external controller to instruct the implantable stimulator device to provide stimulation, tracking the provided stimulation and determine an amount of provided stimulation, determining a difference between the prescribed amount of stimulation and the amount of provided stimulation, wherein the difference indicates the amount of stimulation remaining on the prescription and/or an amount of the prescription used, and using the external controller to provide an indication of the difference. According to some embodiments, the prescribed amount of stimulation is based on a total amount of actively delivered charge to be delivered to the patient. According to some embodiments, the prescribed amount of stimulation is based on a total amount of time that stimulation is to be provided to the patient. According to some embodiments, the prescribed amount of stimulation is based on a total number of boluses of stimulation to be delivered to the patient. According to some embodiments, each bolus of stimulation comprises a specified duration during which stimulation is to be delivered to the patient. According to some embodiments, each bolus of stimulation comprises an amount of actively driven charge to be delivered to the patient. According to some embodiments, using the external controller to provide an indication of the difference comprises displaying an indication of the difference on a user interface of the external controller. According to some embodiments, using the external controller to provide an indication of the difference comprises sending a message to a remote location. According to some embodiments, receiving a prescription at the external controller comprises receiving the prescription from a clinician programmer. According to some embodiments, the steps of receiving a prescription, tracking the provided stimulation, and determining a difference between the prescribed amount of stimulation and the amount of provided stimulation are performed by the implantable stimulator device. According to some embodiments, the steps of receiving a prescription, tracking the provided stimulation, and determining a difference between the prescribed amount of stimulation and the amount of provided stimulation are performed by the external controller.

A system for providing a prescribed amount of stimulation to a patient using an implantable stimulator device that is implantable in the patient and an external controller configured to control the implantable stimulator device is described herein. According to some embodiments, the system is configured to: receive a prescription for stimulation, wherein the prescription quantifies the prescribed amount of stimulation to be provided by the implantable stimulator device, provide stimulation, track the provided stimulation and determine an amount of provided stimulation, determine a difference between the prescribed amount of stimulation and the amount of provided stimulation, wherein the difference indicates the amount of stimulation remaining on the prescription and/or an amount of the prescription used, and provide an indication of the difference. According to some embodiments, the system further comprises a clinician programmer configured to: determine the prescription for stimulation, and transmit the prescription for stimulation to the external controller. According to some embodiments, determining the prescription for stimulation comprises: receiving a stimulation program comprising one or more parameters of a stimulation waveform, receiving one or more inputs indicating an amount of stimulation to be provided to the patient, and calculating the prescription for stimulation based on the stimulation program and the one or more inputs.

Also disclosed herein is a non-transitory computer-readable medium executable on an external controller configured to communicate with an implantable stimulator device, comprising instructions, which when executed by the external controller, configure the controller to: receive a prescription for stimulation, wherein the prescription quantifies a prescribed amount of stimulation to be provided by the implantable stimulator device, instruct the implantable stimulator device to provide stimulation, track the provided stimulation and determine an amount of provided stimulation, determine a difference between the prescribed amount of stimulation and the amount of provided stimulation, wherein the difference indicates the amount of stimulation remaining on the prescription and/or an amount of the prescription used, and provide an indication of the difference.

Also disclosed herein is a method for providing stimulation to a patient using an implantable stimulator device and an external controller configured to control the implantable stimulator device, the method comprising: determining a bolus of stimulation therapy, wherein the bolus comprises a duration during which stimulation is applied and after which stimulation is terminated, using the external controller to instruct the implantable stimulator device to issue a bolus of stimulation therapy. According to some embodiments, determining a bolus of stimulation therapy comprises: issuing a plurality of trial boluses, wherein each trial bolus comprises a different duration, receiving an indication of effectiveness of each of the trial boluses, and based on the indications of effectiveness, determining the best bolus.

Also disclosed herein is a method for providing stimulation to a patient using an implantable stimulator device and an external controller configured to control the implantable stimulator device (ISD), the method comprising: tracking instances when a patient uses the external controller to instruct the implantable stimulator device to issue a bolus of stimulation, wherein the bolus of stimulation comprises active stimulation for a first period of time and wherein after the first period of time the ISD provides no stimulation for a second period of time, correlating the instances with one or more predictors indicative of a need for stimulation, determining an occurrence of one or more of the predictors, and in response to the occurrence, either prompting the patient to issue a bolus of stimulation or automatically issuing a bolus of stimulation. According to some embodiments, the one or more predictors comprises a time of day. According to some embodiments, the one or more predictors is selected from the group consisting of a heartrate measurement, a blood pressure measurement, an activity level, a postural measurement, and a weather condition. According to some embodiments, the first period of time is ten minutes to thirty minutes. According to some embodiments, the second period of time is thirty minutes to twelve hours.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 1 shows an Implantable Pulse Generator (IPG) useable for Spinal Cord Stimulation (SCS), in accordance with the prior art.

FIG. 2 shows an example of stimulation pulses producible by the IPG, in accordance with the prior art.

FIG. 3 shows use of an External Trial Stimulator (ETS) useable to provide stimulation before implantation of an IPG, in accordance with the prior art.

DETAILED DESCRIPTION

Figure 4:
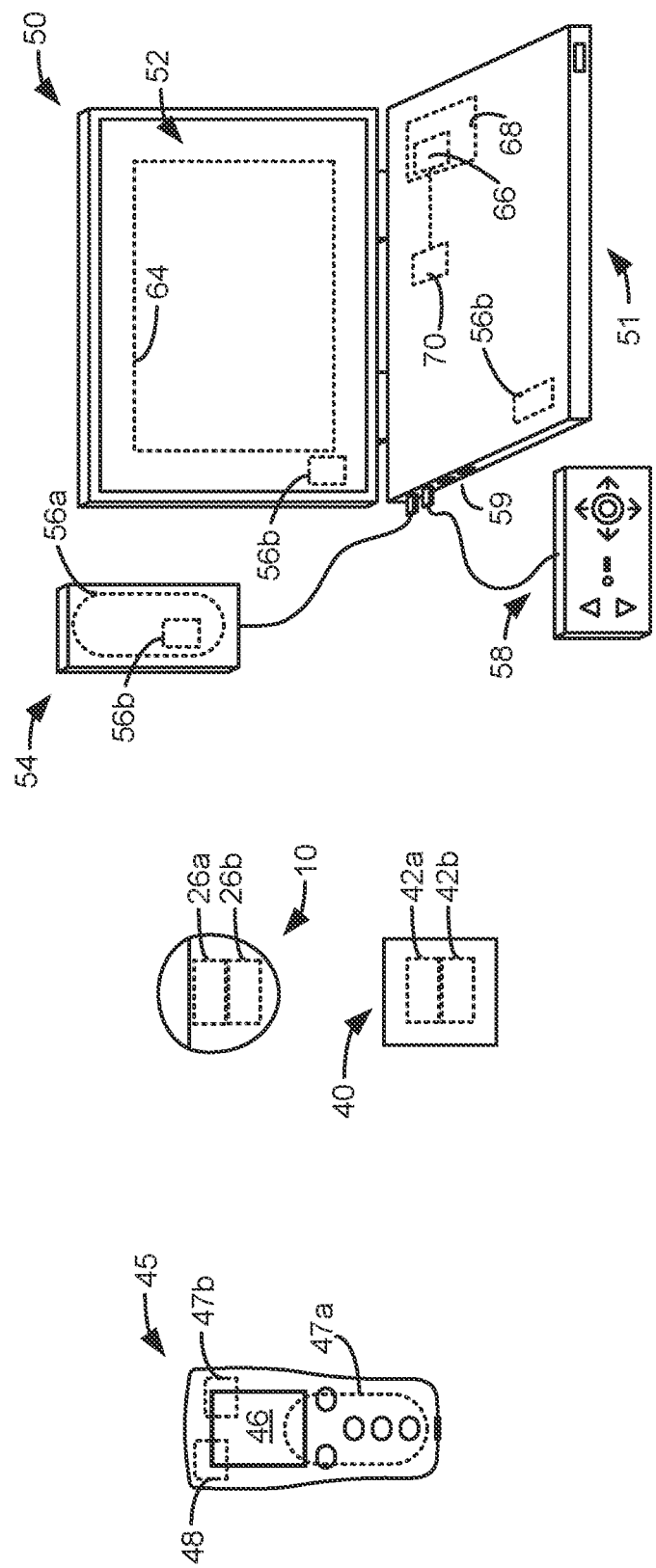
FIG. 4 shows various external devices capable of communicating with and programming stimulation in an IPG and ETS, in accordance with the prior art.

Generally, when a patient has been identified as a candidate for neuromodulation therapy, such as spinal cord stimulation (SCS), the patient receives one or more surgically implanted electrode leads (such as leads 15, FIG. 1). The leads may then be connected to an external trial stimulator (ETS 40, FIG. 4), which allows the patient and his clinician to experiment with different stimulation parameters to try and find a stimulation program that alleviates the patient's symptoms (e.g., pain). If the trial stimulation proves successful, the patient may receive a fully implanted IPG (10, FIG. 1). The patient will typically also receive an external controller (45, FIG. 4), which may be programmed with one or more stimulation programs comprising the parameters that have been determined to be most effective. The external controller allows the patient to select the stimulation programs and also allows them to control various parameters of their therapy, such as stimulation intensity, duration, etc. Under current paradigms, the patient is simply released and they can self-administer therapy at will without returning to the physician for review of effectiveness or follow-up.

The inventors have recognized deficiencies with this treatment paradigm. For one, simply releasing the patient without further scheduled follow-ups may be a missed opportunity for further evaluation and optimization of the patient's therapy. This is in contrast to typical pharmaceutical treatment regimens in which a clinician prescribes a finite number of doses of a drug and requires a follow-up visit to refill the prescription.

Another problem with the present SCS treatment paradigm of allowing the patient the unfettered ability to self-medicate is that the patient may overuse stimulation and develop a tolerance to their stimulation. Overstimulation can reduce the effectiveness of therapy even in the absence of other side effects. A patient may increase the frequency and/or intensity of their stimulation in an effort to compensate for a decrease in the effectiveness of their therapy. But such increases in stimulation can actually negatively impact the patient's therapy because they accelerate the rate at which the patient develops a tolerance to the stimulation. An ideal system would enable a clinician to manage the use of stimulation so that the patient does not overuse the stimulation and reduce the therapy effectiveness.

Disclosed herein are systems and methods that enable a clinician to prescribe a set amount of stimulation that a patient can receive before requiring the patient to seek a further prescription for additional stimulation. According to some embodiments, the prescribed amount of stimulation can be programmed into the patient's external controller or into the IPG. The system may track the amount of stimulation used. The user interface of the external controller may include an indication of the amount of prescribed stimulation remaining. When the patient has used all of the prescribed stimulation, the patient may be directed to make an appointment for a follow-up visit with their clinician to obtain a "refill" for their stimulation prescription. According to some embodiments, the patient's external controller may be an internet connectable device, in which case, the external controller may be configured to send a message to the clinician indicating that the patient has used all of their prescribed stimulation so that the clinician can proactively contact the patient to arrange an appointment.

Figure 7:
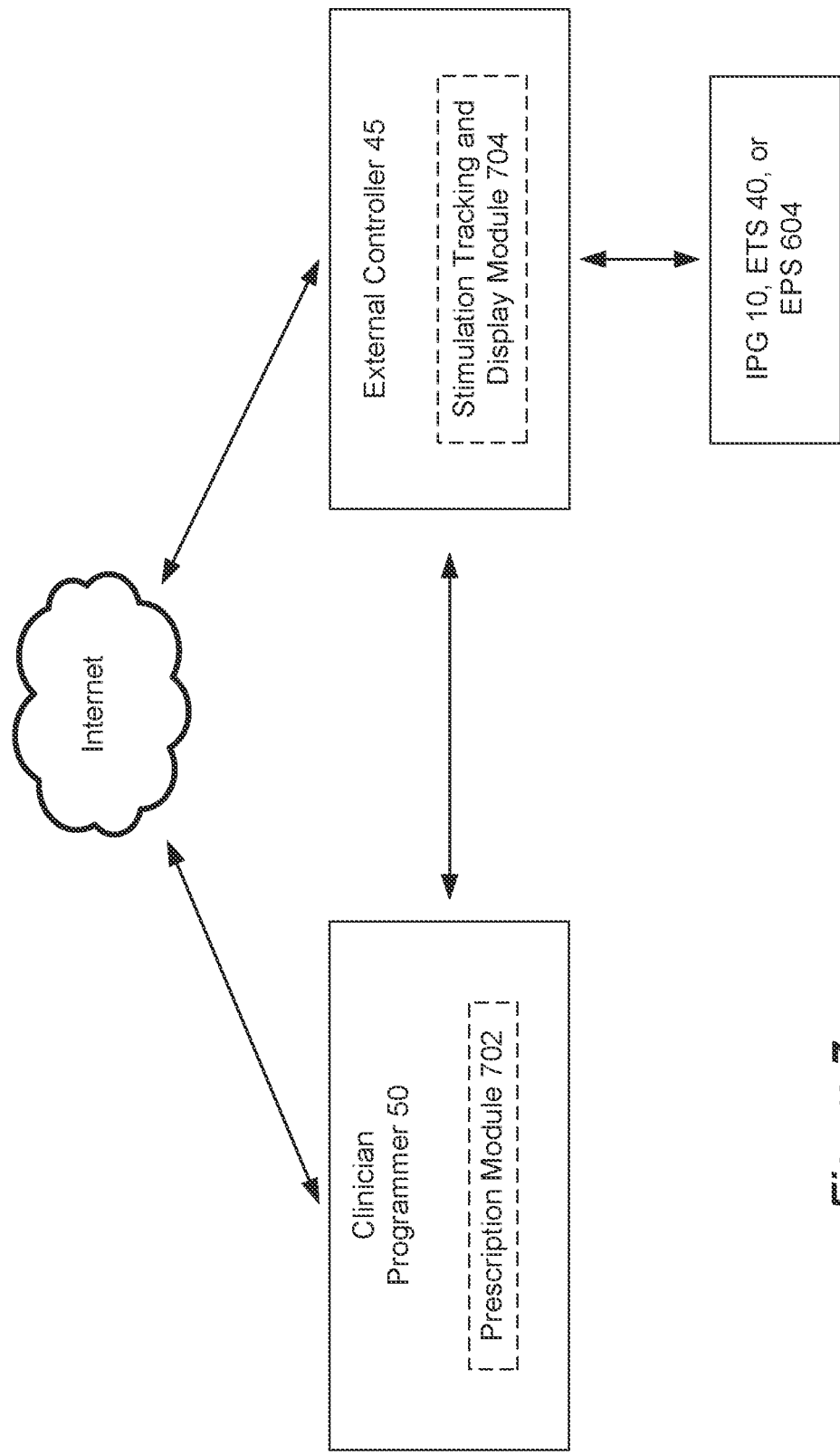
FIG. 7 shows a system for providing a prescribed amount of stimulation.

FIG. 7 illustrates a system 700 for prescribing and monitoring stimulation therapy. The system comprises a clinician programmer 50, which includes the functionality described above. In addition, the clinician programmer 50 comprises one or more therapy prescription modules 702, which are configured to aid the clinician in prescribing an amount of stimulation therapy. The therapy prescription module(s) 702 may be implemented as instructions embodied within non-transitory computer readable media associated with the clinician programmer 50 and executable by processing resources (i.e., one or more microprocessors and/or control circuitry) of the clinician programmer. Such execution configures the clinician programmer to perform the functionality of the prescription module 702, which is described in more detail below.

Figure 6:
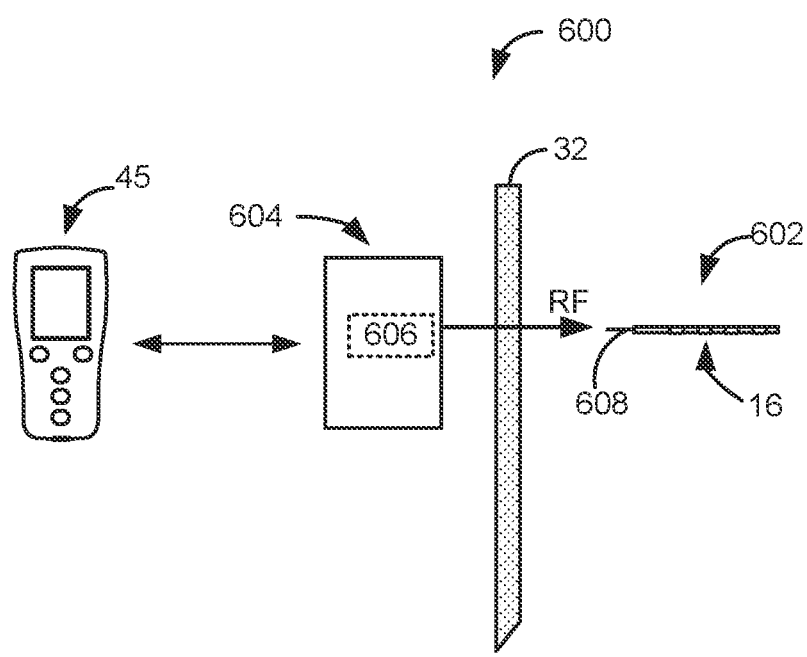
FIG. 6 shows an alternative configuration of an SCS system using an external power supply.

The clinician programmer is configured to transmit the stimulation prescription to the patient's external controller 45 or to the patient's IPG 10. The patient's external controller 45 may have all of the functionality described above for controlling the patient's IPG 10 (FIGS. 1, 3, and 4), ETS (FIG. 4), and/or EPS 604 (FIG. 6). In the illustrated embodiment, the external controller is configured with a stimulation tracking and display module 704 that is configured to receive the stimulation prescription from the clinician programmer 50, track the amount of stimulation used, and display an amount of stimulation remaining on the prescription to the patient. The stimulation tracking and display module 704 may be implemented as instructions embodied within non-transitory computer readable media associated with the external controller 45 and executable by processing resources (i.e., one or more microprocessors and/or control circuitry) of the external controller. Such execution configures the external controller to perform the functionality of the stimulation tracking and display module. According to other embodiments, the prescription and the tracking of the stimulation used may be performed in the IPG, which can communicate the prescription/use information to the patient's external controller for display.

As the prescribed stimulation is used up, the patient may be prompted to schedule an appointment with their clinician to receive a further prescription for additional stimulation. As mentioned above, if the patient's external controller 45 is an internet-connected device, the external controller may be configured to send a notice to the clinician indicating that the patient's prescribed amount of stimulation is depleted or approaching depletion so that the clinician can proactively contact the patient to schedule an appointment. In embodiments wherein the IPG tracks the prescription, the IPG may be configured to send a notice to the patient's personal phone or other computing device (via a Bluetooth connection, for example) informing them that the prescription is depleted or nearing depletion. According to some embodiments, the clinician programmer 50 may be configured to refresh the prescription via an internet connection.

Figure 8:
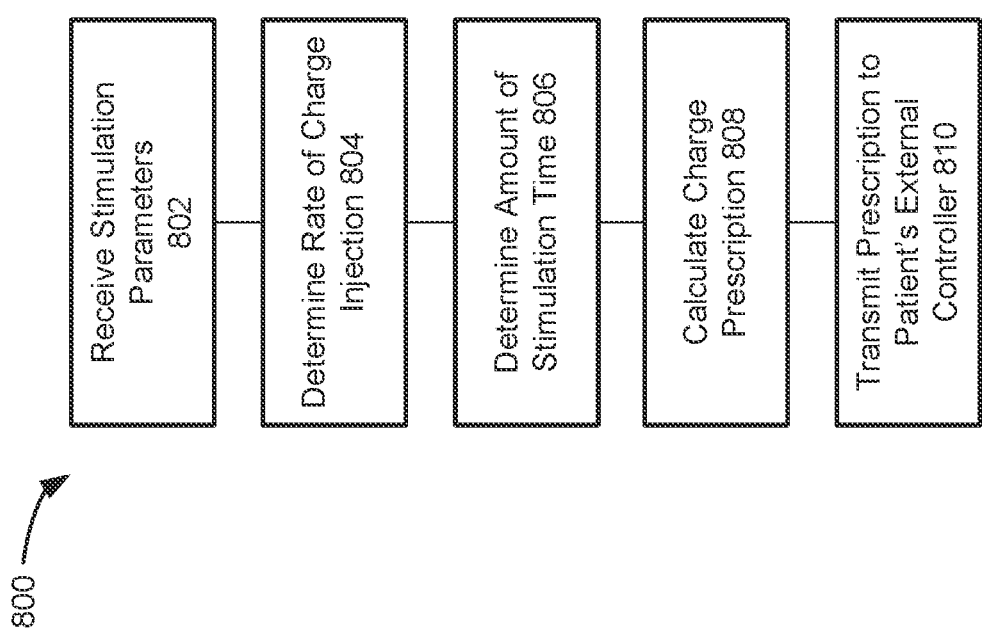
FIG. 8 shows an algorithm for determining a prescription for an amount of stimulation.

According to some embodiments, the prescribed amount of stimulation can be set as a total amount of actively delivered charge. FIG. 8 illustrates an example of an embodiment of an algorithm 800 that a clinician may use to determine and prescribe an amount of total charge to prescribe for a patient's therapy. The algorithm 800 may implemented as a program in the clinician programmer 50 (FIG. 4), for example, as a component of a prescription module 702 (FIG. 7). The algorithm assumes that the clinician and patient have determined one or more stimulation programs that are expected to be beneficial for the patient. The process of determining appropriate stimulation programs may be referred to as a fitting process.

At step 802 of the algorithm, the algorithm receives the stimulation parameters for the one or more programs that have been determined during the fitting process. For example, assume that the clinician has determined that the patient experiences pain relief when the patient is stimulated using a simple biphasic stimulation waveform, such as the waveform illustrated in FIG. 2. Assume that the waveform has a frequency of 100 Hz, an amplitude of 3 mA, and a pulse width of 100 µs. All of those parameters are provided to the algorithm at step 802. Of course, the stimulation program could be more complex, for example, involving complex pulse shapes, pulse patterns, and the like. Moreover, multiple programs may be determined during the fitting process. But for simplicity, a single simple biphasic waveform is considered here.

At step 804 the algorithm analyzes the stimulation waveforms contained in the defined stimulation program and calculates the rate of charge injection into the patient (i.e., the amount of actively driven charge provided as a function of time) when executing the stimulation program. For example, the stimulation parameters listed above would nominatively pass 0.108 Coulombs of charge per hour when executing the stimulation program.

At step 806 the algorithm receives input indicating an amount of time that stimulation should ideally be applied before the patient returns for a follow-up visit. For example, assume that the clinician believes that the patient should generally applying stimulation for 12 hours per day and the clinician would like for the prescription to be adequate for six months, after which, the patient should return for a follow-up visit. The clinician would enter those time parameters into the user interface of the clinician programmer, for example, as part of the prescription module 702 (FIG. 7).

At step 808 the algorithm calculates a charge prescription. In this simple example, the calculation is relatively straight forward. The values of the programmed stimulation parameters—amplitude, frequency, and pulse width—provide actively driven charge at a rate of 0.108 Coulombs per hour. That rate correlates to 1.3 Coulombs per day if the patient applies stimulation for 12 hours per day, which further correlates to 232 Coulombs over six months (180 days). Thus, the prescription will be calculated as 232 Coulombs, based on the parameters provided by the clinician. It should be appreciated that since the algorithm has access to the stimulation waveform program and the relevant stimulation parameters, the algorithm can be configured to calculate the actively driven charge for generally any duration of stimulation, even for complex waveforms.

At step 810, the calculated charge prescription can be transmitted from the clinician programmer to the patient's external controller. It should be noted that while the illustrated algorithm 800 computes a stimulation prescription based on Coulombs of charge, neither the clinician nor the patient may be interested in the absolute value of Coulombs, per se. Instead, the clinician can simply prescribe stimulation based on the particular stimulation parameters, the amount of stimulation per day, and the ideal length of time before a follow-up appointment. Given those data points, the algorithm 800 calculates a "charge prescription." It should also be noted that the prescription may be determined on the basis of total energy or some other metric that relates to an amount of stimulation. For example, the clinician may prescribe stimulation on the basis of time, time per day, or boluses of stimulation, which is discussed in more detail below. The prescription module 702 executed on the clinician programmer may be configured with different options for allowing the clinician to prescribe stimulation.

Figure 9:
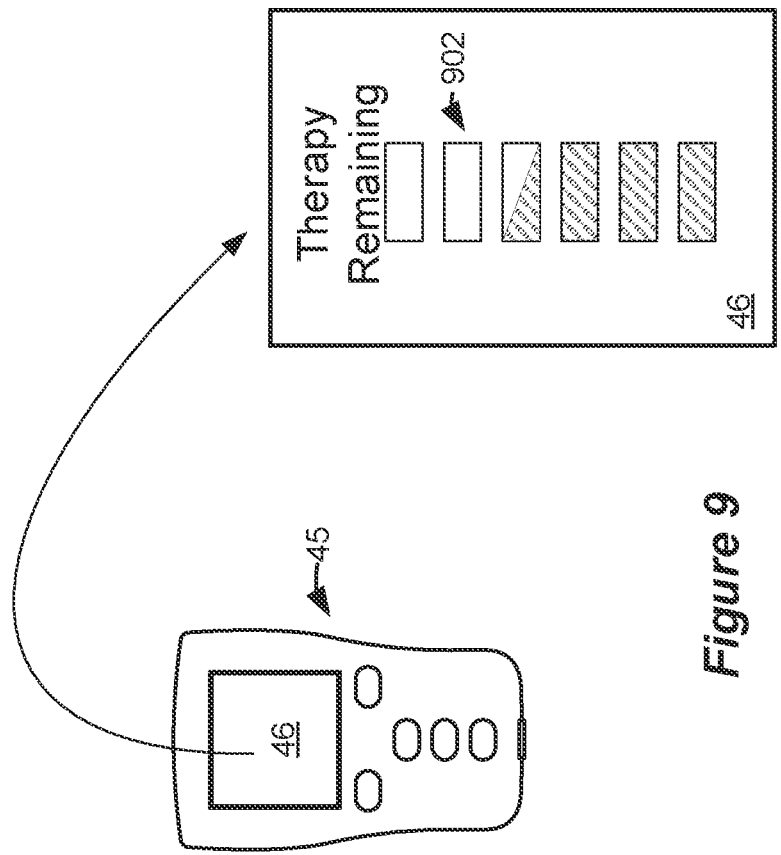
FIG. 9 shows a user interface for tracking prescribed stimulation.

FIG. 9 illustrates an embodiment of an external controller 45 having a display 46. The external controller may comprise a stimulation tracking and display module 704 (FIG. 7) configured to receive the stimulation prescription from the physician controller and to account for the amount of charge used during stimulation. The amount of charge remaining for the patient's prescription may be displayed on the display 46 of the patient's external controller. For example, in the illustrated embodiment, the external controller presents a gauge 902 indicating the amount of therapy remaining on the prescription. As the patient uses their SCS system their external controller can track the amount of charge used and may display the amount of charge remaining on the prescription (either as charge or some variable related to charge). When the patient's prescribed charge is depleted or approaching depletion, they may be prompted to schedule a follow-up appointment with the clinician. The patient may use their prescribed amount of stimulation at a faster rate than anticipated, for example, by applying stimulation more frequently or by using a greater amplitude or pulse width. In that case, the patient will be prompted to schedule a follow-up sooner than the anticipated six months. This may afford the patient and clinician to explore reasons that the patient is requiring more stimulation than anticipated.

According to some embodiments, stimulation may be provided in discreet chunks of stimulation, referred to as a "bolus" of stimulation. A bolus of stimulation may be thought of as analogous to a single dose of stimulation, similar to a dose of a pharmaceutical agent. For example, a bolus may comprise stimulation for a first period of time, such as 10 minutes of stimulation (or minutes, or 1 hour, etc.). After a bolus is issued further stimulation is not provided until another bolus is issued. Typically, the time period between boluses (i.e., a second period of time) is on the order of at least minutes, or hours, for example. For example, according to some embodiments, the second period of time may be thirty minutes to twelve hours. However, according to some embodiments, a patient could issue themselves another bolus immediately following a first bolus, just as patient could take a second dose of a pharmaceutical immediately following a first dose.

It has been observed that some patients respond well to bolus mode treatment. A patient may initiate a bolus of stimulation when they feel pain coming on. Some patients experience extended pain relief, up to several hours or more, following receiving a bolus of stimulation. According to some embodiments, a clinician may prescribe stimulation therapy based on a number of boluses of stimulation. To draw an analogy to a pharmaceutical prescription, a clinician might prescribe a given number of boluses of stimulation to a patient per day for a certain duration. For example, a clinician might prescribe five 30-minute boluses of stimulation per day for three months, after which the patient returns to the clinician for a follow-up evaluation.

Figure 5:
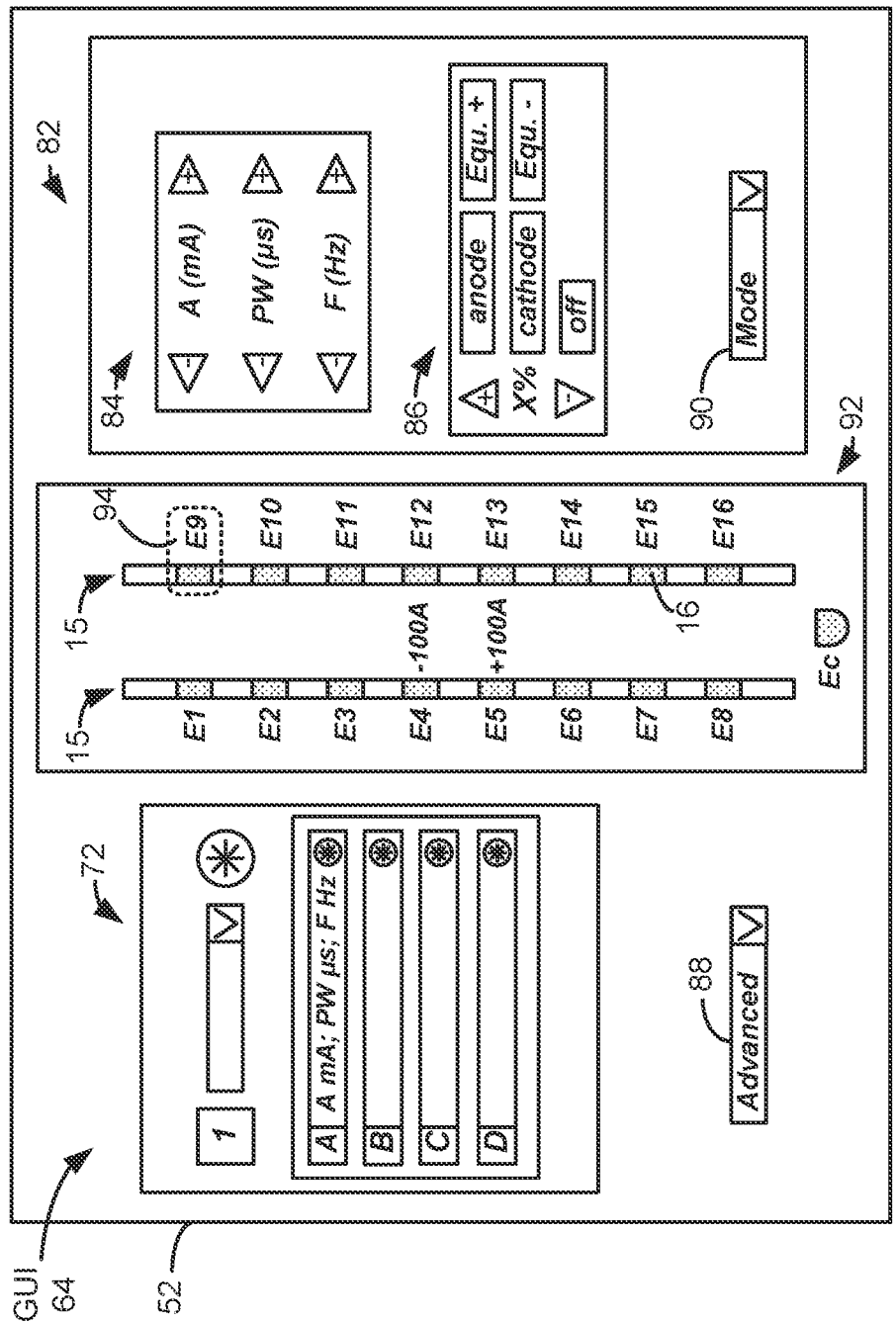
FIG. 5 shows a Graphical User Interface (GUI) of a clinician programmer external device for setting or adjusting stimulation parameters, in accordance with the prior art.
Figures 10, 11:
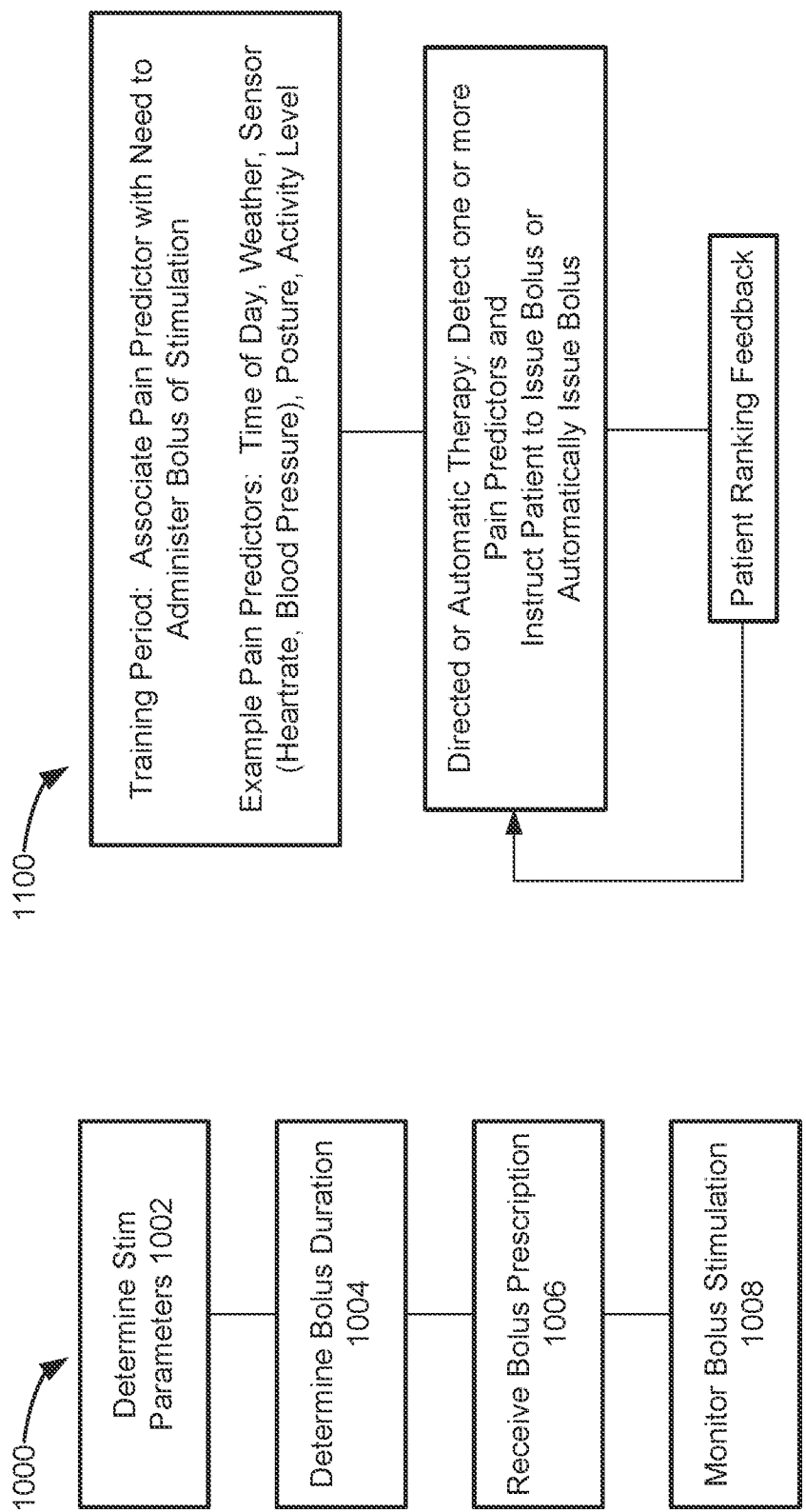
FIG. 10 shows an algorithm for determining and monitoring bolus-mode stimulation.
FIG. 11 shows an algorithm for preemptively issuing a bolus of stimulation.

FIG. 10 illustrates an example of a method 1000 of determining and prescribing a bolus mode treatment. At step 1002, appropriate stimulation parameters are determined for the patient. This process is generally done in a fitting session with the aid of a clinician programmer 50 (FIGS. 4, 5, and 7), as described above. Assume that, during the fitting process, the clinician has determined one or more stimulation programs that alleviate the patient's pain and also assume that the clinician believes that the patient may respond well to bolus mode treatment. Having determined optimum stimulation parameters, the patient may be released with an implanted IPG (or ETS or EPS) and their external controller 45 to determine an appropriate time period corresponding to a bolus of stimulation. For example, the stimulation tracking and display module 704 in the patient's external controller may be programmed with a bolus algorithm configured to help the patient and clinician determine an appropriate bolus of stimulation. The goal is to determine a time period of stimulation that achieves long-lasting pain relief. When the patient experiences the onset of pain, they may activate a trial bolus. For example, a trial bolus may comprise 5 minutes of stimulation using the patient's optimum stimulation parameters. The patient will receive a bolus of stimulation, after which the stimulation will terminate. The patient may then be asked to periodically rate their pain relief (for example, every hour after the administration of the trial bolus) using the interface of their external controller. Over a period of days or weeks, different time periods of stimulation may be tried to determine a minimum time period that provides the longest-lasting pain relief. Various optimization criteria may be used for making the determination of an optimum bolus, depending on the patient's and the clinician's preferences. Alternatively, the clinician may simply decide what time period of stimulation will constitute a bolus of stimulation at step 1004.

Having determined an appropriate stimulation duration corresponding to a bolus of stimulation, the patient may receive a prescription for a number of boluses (step 1006). According to some embodiments, the patient may return to their clinician following the bolus determination step (step 1004) so that the clinician can program the patient's external controller with a prescription for a given number of boluses. According to some embodiments, if the patient's external controller is an internet-connected device, the patient may not need to return to the clinician. Instead, the patient's external controller may transmit the bolus duration to the clinician programmer via an internet connection and the clinician programmer may transmit the bolus prescription to the patient's external controller via the internet connection. Once the patient's external controller is programmed with a bolus prescription, the external controller can monitor the number of boluses used (Step 1008). The number of boluses remaining on the patient's prescription may be displayed on the external controller. Once the patient has used the prescribed number of boluses, the patient may be prompted to schedule a follow-up visit with the clinician.

It should be noted that, according to some embodiments, the clinician may simply prescribe a certain stimulation duration as a bolus without using an algorithm such as the algorithm 1000. For example, the clinician may simply decide that a bolus of stimulation will correspond to ten minutes of stimulation. Alternatively, according to some embodiments, the patient's external controller may be programmed with an algorithm that helps the patient determine an appropriate bolus of stimulation without approval of the clinician. For example, the patient's external controller may be programmed with a bolus calibration duration, for example, two weeks, during which the patient is prompted to rank therapy using different bolus durations. After the calibration duration, the external controller considers the determined optimum duration of stimulation as a bolus of stimulation. The external controller may then begin tracking the number of boluses remaining for the patient's prescription. For example, the GUI of the external controller may inform the patient that they have x of y boluses remaining.

According to some embodiments, the patient's external controller may be programmed with one or more algorithms that attempt to optimize when a bolus of stimulation should issue. When the algorithm determines that a bolus should be issued, the patient's external controller may alert the patient to administer themselves a bolus of stimulation. Such an embodiment may be particularly useful for patients using an RF system (i.e., a system without an implanted IPG). A patient using such a system can receive a notice or alert when it is time to receive a bolus of stimulation and the patient can then arrange their external power supply (EPS) appropriately an administer themselves a bolus. Alternatively, a patient using a system with a traditional IPG can use their external controller to cause the IPG to issue a bolus of stimulation when they receive an alert that it is time to issue a bolus. According to some embodiments, the external controller may simply instruct the IPG to issue a bolus automatically without the patient instructing the external controller to so. According to some embodiments, the patient may receive an alert on their personal computing device, such as a personal phone, that it is time to take a bolus.

FIG. 11 illustrates an example of an algorithm 1100 for predicting when a bolus should issue. The algorithm 1100 comprises a "training period" during which the algorithm attempts to correlate one or more "pain predictors" with instances that the patient issues themselves a bolus. The pain predictor is a predictor indicative of a need for stimulation. Examples of pain predictors may include the time of day, the weather, the patient's activity level, or one or more physiological parameters of the patient, such as heartrate, blood pressure, posture, or the like. For example, during the training period the algorithm may determine that the patient tends to issue themselves a bolus at certain times during the day. The algorithm may therefore determine that those are the times of day that the patient tends to experience pain. Likewise, the algorithm may determine that the patient tends to administer a bolus when they transition from sitting to standing, or vice-versa. Such postural changes may be detected using measured evoked compound action potentials (ECAPs) or other sensed neural responses, as described in U.S. Patent Application Publication 2022/0323764. Alternatively (or additionally), postural changes and/or patient activity level may be determined using accelerometers. Physiological parameters, such as heartrate, blood pressure, and the like may be determined using one or more physiological sensors associated with the patient. According to some embodiments, pain predictors such as activity level, weather, posture, and the like, may be determined based on patient input, for example, via an application running on their external controller or other external device in communication with their external controller. Alternatively, to determine weather conditions, the patient's external controller (or other external device in communication with the external controller) may be configured to obtain weather information via internet weather data. The training period may be a few days or a few weeks, for example.

Once the training period is concluded, the algorithm may proceed to a directed therapy or automatic therapy regime wherein the algorithm monitors for one or more of the pain predictors. When a pain predictor is detected the algorithm may either instruct the patient to preemptively issue themselves a bolus or may automatically issue the patient a bolus without patient input. As mentioned above, embodiments wherein the patient is instructed to issue themselves a bolus are particularly useful for patients with an RF system that does not use an implanted IPG.

According to some embodiments, the patient may be prompted for feedback ranking the effectiveness of the attempted therapy programs, for example, by selecting a ranking on the user interface of their external controller. Based on the patient feedback, the algorithm may attempt to optimize the algorithm.

Figure 12A:
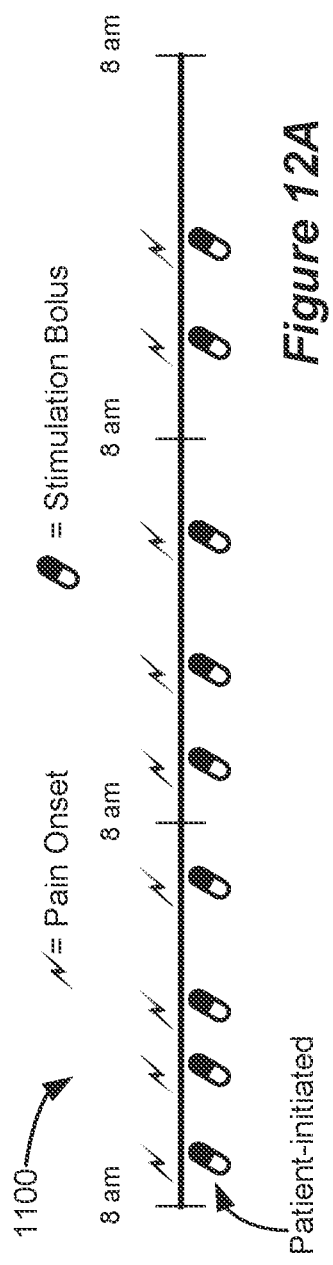
FIGS. 12A-12C show the use of an algorithm for preemptively issuing a bolus of stimulation.
Figure 12B:
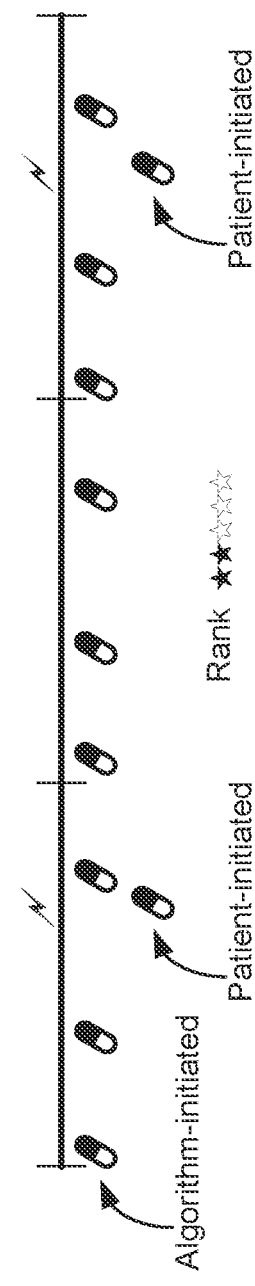
Figure 12C:
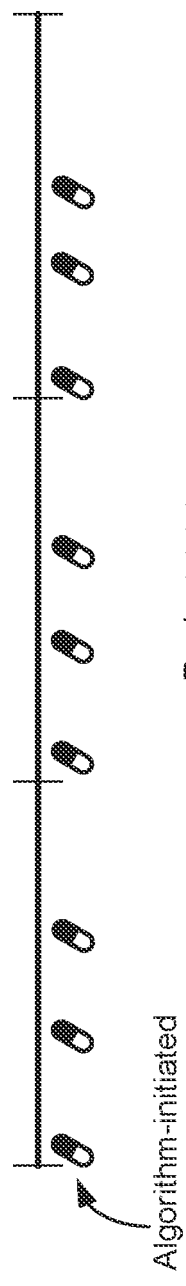

FIGS. 12A-12C illustrate an example of the algorithm 1100 for determining when to preemptively issue a bolus of stimulation. The example algorithm 1100 illustrated in FIG. 12A-12C uses the time of day as the pain predictor and also uses patient feedback to optimize the algorithm. FIG. 12A illustrates a training period where the patient self-administers a bolus (represented by a capsule in FIGS. 12A-12C) each time they perceive the onset of pain (represented by a lighting bolt). According to some embodiments, an algorithm may track the times that the patient issues themselves a bolus and then attempt to preemptively issue a bolus before the patient experiences pain onset. Notice in FIG. 12A that the patient's pain onset events are weighted more heavily to the early part of the day. Assume that the algorithm 1100 has tracked the three days of therapy illustrated in FIG. 12A. FIG. 12B illustrates an attempt by the algorithm to preemptively issue boluses of therapy over a three-day period based on the boluses that the patient administered in FIG. 12A. For example, in FIG. 12A, the patient, on average, administered three boluses per day. So, in FIG. 12B, the algorithm 1100 automatically provides those boluses each day at time periods that best match those in FIG. 12A. The patient can continue to self-administer boluses and the algorithm 1100 can continue to optimize the timing of automatically providing boluses. For example, on days one and three, the preemptively issued boluses of were not sufficient to completely curtail the patient's pain and the patient had to self-administer an extra bolus on those days. In FIG. 12B, the patient has rated the therapy two-out-of-five. In FIG. 12C, the algorithm has attempted to improve the therapy by issuing the third bolus earlier in the day, corresponding to the self-administered boluses. The patient has not had to self-administer a bolus of stimulation over a three-day period and has ranked the therapy a four-out-of-five. The algorithm 1100 may thus determine that the timing determined in FIG. 10C may be used as ongoing therapy.

Bolus mode therapy may provide several advantages compared to traditional continuous therapy. For example, bolus mode therapy may decrease the chances that the patient overuses stimulation, thereby developing a tolerance to the therapy. Also, bolus mode therapy is particularly well suited for RF stimulation systems, such as described above with reference to FIG. 6. Since a bolus of stimulation is only applied for a finite duration of time, a patient using an RF system need only have access to their external power supply during the time they are receiving a bolus of stimulation.

Various aspects of the disclosed techniques, including processes implementable in the IPG or ETS, or in external devices such as the clinician programmer and/or the external controller can be formulated and stored as instructions in a computer-readable media associated with such devices, such as in a magnetic, optical, or solid-state memory. The computer-readable media with such stored instructions may also comprise a device readable by the clinician programmer or external controller, such as in a memory stick or a removable disk, and may reside elsewhere. For example, the computer-readable media may be associated with a server or any other computer device, thus allowing instructions to be downloaded to the clinician programmer system or external controller or to the IPG or ETS, via the Internet for example. The various algorithms described herein and stored in non-transitory computer readable media can be executed by one or more microprocessors and/or control circuitry configured within the relevant device, thereby causing the device to perform the steps of the algorithm(s).

Note that some of the applications to which this present disclosure claim priority, which are incorporated by reference above, are directed to concepts (e.g., picking optimal stimulation parameters, and in particular stimulation parameters that cause sub-perception at lower frequencies) that are relevant to what is disclosed. Techniques in the present disclosure can also be used in the context of these priority applications. For example, the prescribed stimulation may be determined and optimized using the techniques described in some of the priority applications. Also, the parameters of the bolus stimulation may be determined and optimized using the techniques described in some of the priority applications.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for providing electrical stimulation to a patient's spinal cord using an implantable stimulator device (ISD) connected to one or more electrode leads implanted in the patient's spinal column, each electrode lead comprising a plurality of electrodes, and an external controller configured to control the ISD, the method comprising:
   during a training period:
   tracking instances when a patient issues themselves a bolus of stimulation,
   correlating the instances with one or more predictors indicative of a need for a bolus of stimulation,
   subsequent to the training period:
   during a period that no stimulation is provided to the patient, determining an occurrence of one or more of the predictors, and
   in response to the occurrence, either prompting the patient to issue a preemptive bolus of stimulation or automatically issuing a preemptive bolus of stimulation, wherein the bolus of stimulation comprises active stimulation for a first period of time and wherein after the first period of time the ISD provides no stimulation for a second period of time.

2. The method of claim 1, wherein the first period of time is ten minutes to thirty minutes.

3. The method of claim 1, wherein the second period of time is thirty minutes to twelve hours.

4. The method of claim 1, wherein the one or more predictors comprises a time of day.

5. The method of claim 1, wherein the one or more predictors is selected from the group consisting of a heartrate measurement, a blood pressure measurement, an activity level, a postural measurement indicating a change in posture, and a weather condition.

6. The method of claim 5, wherein the one or more predictors comprises a postural measurement comprising measurement of evoked compound action potentials.

7. The method of claim 1 wherein the instances when the patient issues a bolus of stimulation do not correspond to previously scheduled boluses.

8. The method of claim 1, wherein tracking the one or more patient-initiated indications of pain comprises using the external controller to track the patient-initiated indications of pain.

9. The method of claim 1, wherein prompting the patient to issue a preemptive bolus of stimulation comprises providing a notice to the patient via the external controller.

10. The method of claim 1, further comprising using a correlation of the patient-initiated indications of pain with one or more predictors indicative of a need for stimulation to adjust a preexisting schedule of stimulation to provide an adjusted schedule of stimulation.

11. The method of claim 10, further comprising receiving a patient ranking of the adjusted schedule of stimulation.

12. The method of claim 11, further comprising using the patient ranking of the adjusted schedule of stimulation to determine whether to further adjust the adjusted schedule of stimulation.

13. A system for providing electrical stimulation to a patient's spinal cord using an implantable stimulator device (ISD) connected to one or more electrode leads implanted in the patient's spinal column, each electrode lead comprising a plurality of electrodes, the system comprising:

an external controller configured to control the ISD, wherein the ISD comprises control circuitry configured to perform a method comprising:
during a training period:
tracking instances when a patient issues themselves a bolus of stimulation,
correlating instances with one or more predictors indicative of a need for a bolus of stimulation,
subsequent to the training period:
during a period that no stimulation is provided to the patient, determining an occurrence of one or more of the predictors, and
in response to the occurrence, either prompting the patient to issue a preemptive bolus of stimulation or automatically issuing a preemptive bolus of stimulation, wherein the bolus of stimulation comprises active stimulation for a first period of time and wherein after the first period of time the ISD provides no stimulation for a second period of time.

14. The system of claim 13, wherein the one or more predictors indicative of a need for stimulation is selected from the group consisting of a time of day, a heartrate measurement, a blood pressure measurement, an activity level, a postural measurement indicating a change in posture, and a weather condition.

15. The system of claim 13, wherein the instances when the patient issues a bolus of stimulation do not correspond to previously scheduled boluses.

16. The system of claim 13, wherein the method further comprises using a correlation of the patient-initiated indications of pain with one or more predictors indicative of a need for stimulation to adjust a preexisting schedule of stimulation to provide an adjusted schedule of stimulation.

* * * * *